United States Patent [19]

Ross et al.

[11] 4,306,152

[45] Dec. 15, 1981

[54] OPTICAL FLUID ANALYZER

[75] Inventors: Thaddeus C. Ross, Santa Barbara; Donald E. Burrows, Montecito, both of Calif.

[73] Assignee: Anarad, Inc., Santa Barbara, Calif.

[21] Appl. No.: 59,798

[22] Filed: Jul. 23, 1979

[51] Int. Cl.³ .............................................. G01J 1/00
[52] U.S. Cl. .................................... 250/343; 250/345
[58] Field of Search ............... 250/252, 341, 343, 344, 250/345, 565

[56] References Cited

U.S. PATENT DOCUMENTS

| | | | |
|---|---|---|---|
| 3,562,522 | 2/1971 | Cederstrand et al. | 250/343 |
| 3,979,589 | 9/1976 | Sternberg et al. | 250/252 |
| 4,069,420 | 1/1978 | Ross | 250/341 |
| 4,153,837 | 5/1979 | Ross | 250/343 |

*Primary Examiner*—Alfred E. Smith
*Assistant Examiner*—Janice A. Howell

[57] ABSTRACT

An optical fluid analyzer uses the extent of optical, preferably infrared absorption of a fluid to be analyzed to determine the concentration of a selected constituent of the fluid. A first detector detects light after absorption by the fluid at a wavelength at which the selected constituant has a characteristic absorption for conversion into an electrical signal indicating the concentration of the selected constituant and a background from absorption of other constituents of the fluid for a measurement processing channel. A second detector correspondingly converts light after absorption by the fluid, but at a different wavelength at which the absorption at least approximates the background absorption alone for a neutral processing channel. The signals from the measurement and neutral processing channels are then subtracted to reduce the level of the background signal so that the level of the signal from the characteristic absorption can be more accurately processed to indicate the concentration of the selected constituent. The analyzer further has a first adjusting arrangement requiring ony a readily available, staple fluid to compensate for variations in the analyzer operation and a separate, second adjusting arrangement for presetting the analyzer with a standard fluid. Both the background subtraction and separate adjusting features of the analyzer particularly adapt it for analyzing liquid fluids.

5 Claims, 3 Drawing Figures

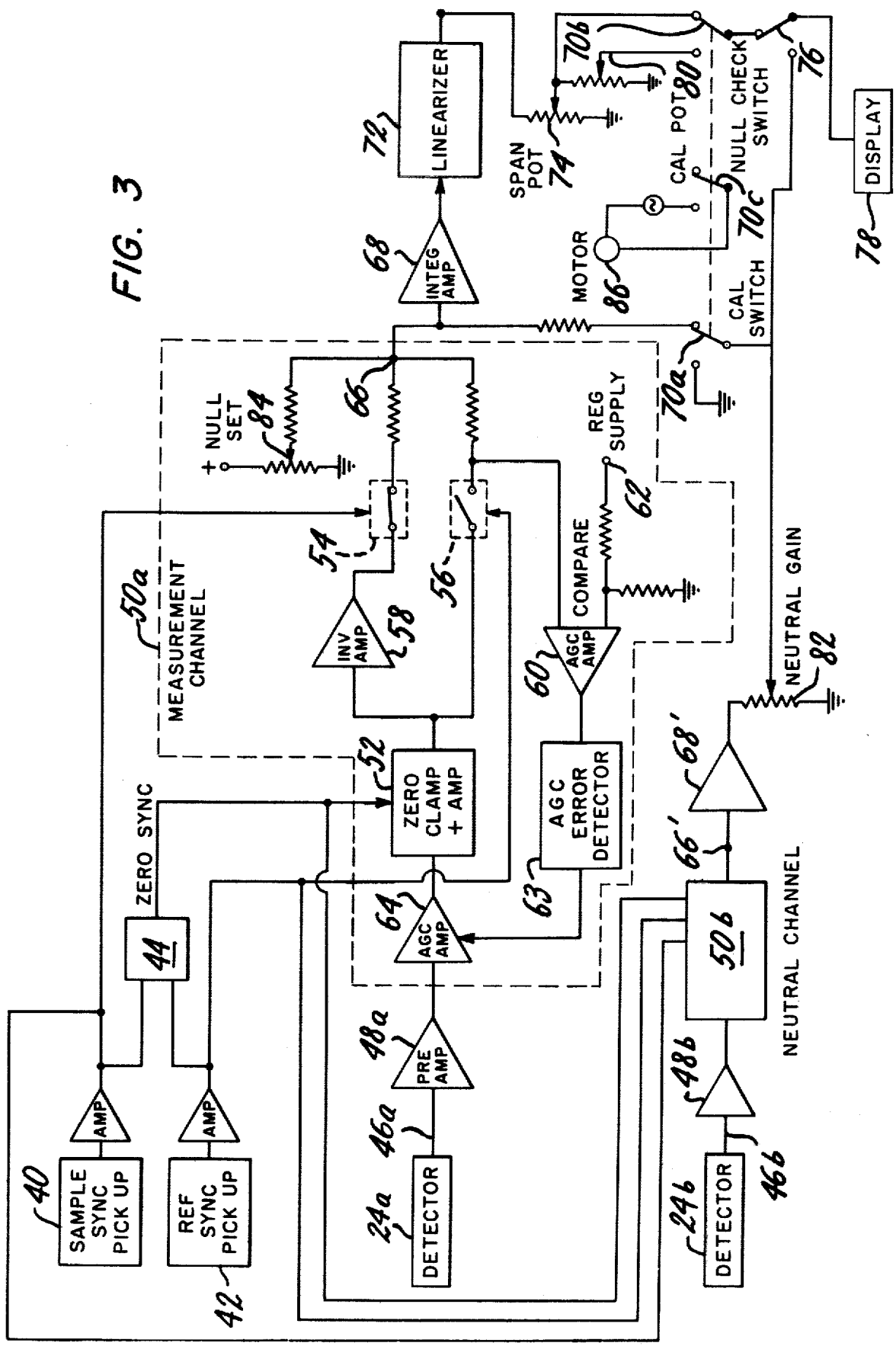

OPTICAL FLUID ANALYZER

BACKGROUND OF THE INVENTION

The invention relates to an analyzer for optically determining the concentration of a selected constituent of a fluid.

Optical fluid analyzers for both gas and liquid fluids are known. One, for example, is disclosed in the Assignee's U.S. Pat. No. 4,069,420. The analyzer disclosed in this patent uses the extent of infrared absorption at a wavelength at which a selected constituent of the fluid to be analyzed has a characteristic absorption to indicate the concentration of the constituent.

A rotating chopper disc alternately transmits the infrared light along separate optical paths from a single, infrared source through separate chambers to a single detector, one of the chambers containing the fluid to be analyzed and the other containing a reference specimen of known absorption. Electrical signals from the single detector are processed in synchronism with the path alternation to provide alternate signals corresponding to the absorption in the sample and reference chambers. The alternate signals are then integrated (subtracted) to provide a difference signal which indicates the concentration of the selected constituent in the fluid. Providing the separate optical paths to obtain the separate sample and reference signals for integration tends to cancel the effect fo certain variations in the operation of the analyzer such as variations in the infrared source for more accurate analyses.

In addition, each interval between the alternate, chopped optical signals is used to clamp or re-zero the electrical signal processing and each signal from the reference chamber where the absorption is known is used to restandardize the gain of the electrical signal processing. These three features, the separate optical paths, the zero clamp and the reference gain control, thus each contribute to making the analyzer described in U.S. Pat. No. 4,069,420 highly accurate.

Further refinements to the analyzer disclosed in the beforementioned patent are, however, disclosed in the Assignee's further U.S. Pat. No. 4,153,837. These further refinements relate to barometric pressure compensation, temperature compensation, and calibration display.

Neither of the analyzers disclosed in the patents, however, has an arrangement to minimize the effect of background absorption. The background absorption is the overall or base level of optical absorption of the fluid to be analyzed from which the absorption of the selected constituent departs at its characteristic wavelength to an extent indicating the concentration of the selected constituent. When the level of background absorption is high in relation to the characteristic absorption of the selected constituent, as it is for many liquids because of their turbidity and other properties, accurate measurement of the level of the small change in the absorption at the characteristic wavelength of the constituent selected to be analyzed for determining the constituent concentration becomes very difficult even for high concentrations of the constituent, and more difficult still for low concentrations.

An analyzer which could reduce the background level of the signal to be analyzed could thus be even more accurate than the patented analyzers and particularly useful for analyzing liquids.

Highly accurate analyzers for liquid, particularly, also present a further problem. Because the fluid analyzer must produce a signal the actual or absolute value of which indicates the concentration rather than merely accurate relative signals, aging, temperature or other internal changes in the signal-processing components will affect the analyzer operation. The analyzer therefore has to be periodically reset for accuracy using a standard fluid of known constituent concentration. Pure gases for such standard fluids in gas fluid analyzsis are reasonably available, but standard liquid fluids often require special, difficult preparation and handling and are more difficult to purge from the analyses after use to present greater risk of contaminating subsequent analyzes. An analyzer which could be adjusted for internal changes without using a standard fluid and thus less frequently restandardized with a standard fluid would thus be particularly useful for analyzing liquids.

SUMMARY OF THE INVENTION

It is therefore an object of the invention to provide a more accurate optical analyzer for determining the concentration of a selected constituent of a fluid, and more particularly, a more accurate analyzer for a selected constituent of a fluid such as many liquids having a high background optical absorption.

It is a further object of the invention to provide an analyzer of the concentration of a selected constituent of a fluid which can be adjusted for accuracy without a standard fluid.

To this end, the invention provides an optical fluid analyzer which reduces the affect of background absorption for improved accuracy and allows adjustment for internal changes in the processing components of the analyzer without using a standard fluid. Fluid, as used here, includes both gas and liquid fluids, the analyzer being only particularly useful for analyzing liquids because of their more common high background absorption and greater standard fluid problems.

The analyzer uses the extent of optical, preferably infrared absorption of a selected constituent of the fluid to be analyzed at a wavelength characteristic of the constituent to determine the concentration of the constituent in the fluid. The characteristic optical absorption and the optical absorption at a different wavelength which is selected to at least approximate the background absorption are converted into electrical signals and processed in separate measurement and neutral channels and then subtracted to reduce the background component of the signal. Small values of the concentration-indicating characteristic absorption component of the combined signal are then more accurately determined for more accurately indicating the concentration of the selected constituent.

Separate ways of adjusting (zeroing) the analyzer when only a readily available or staple fluid which does not absorb significantly in relation to the fluid to be analyzed is present in the analyzer and presetting the analyzer with a standard fluid of known absorption are provided. Each adjustment for internal changes in the analyzer processing devices thus does not require the difficult-to-use standard fluid.

DESCRIPTION OF THE DRAWINGS

A preferred embodiment which is intended to illustrate but not to limit the invention will now be described with reference to the drawings in which:

FIG. 3 is a schematic of the electrical components of the preferred embodiment.

DESCRIPTION OF THE PREFERRED EMBODIMENT

The preferred embodiment is an optical fluid analyzer for indicating the concentration of a selected constituant of a fluid to be analyzed, and particularly liquid and other fluids which have a high background or overall optical absorption in relation to the characteristic wavelength optical absorption of the selected constituent, the extent of which characteristic absorption indicates the concentration of the selected constituent in the fluid. Several of the optical-mechanical and electrical components of the preferred embodiment are the same or so substantially similar to components of the optical analyzer disclosed in the Assignee's beforementioned U.S. Pat. No. 4,069,420 that the disclosure thereof is incorporated herein by reference for a more detailed explanation of these components.

Figure 1:
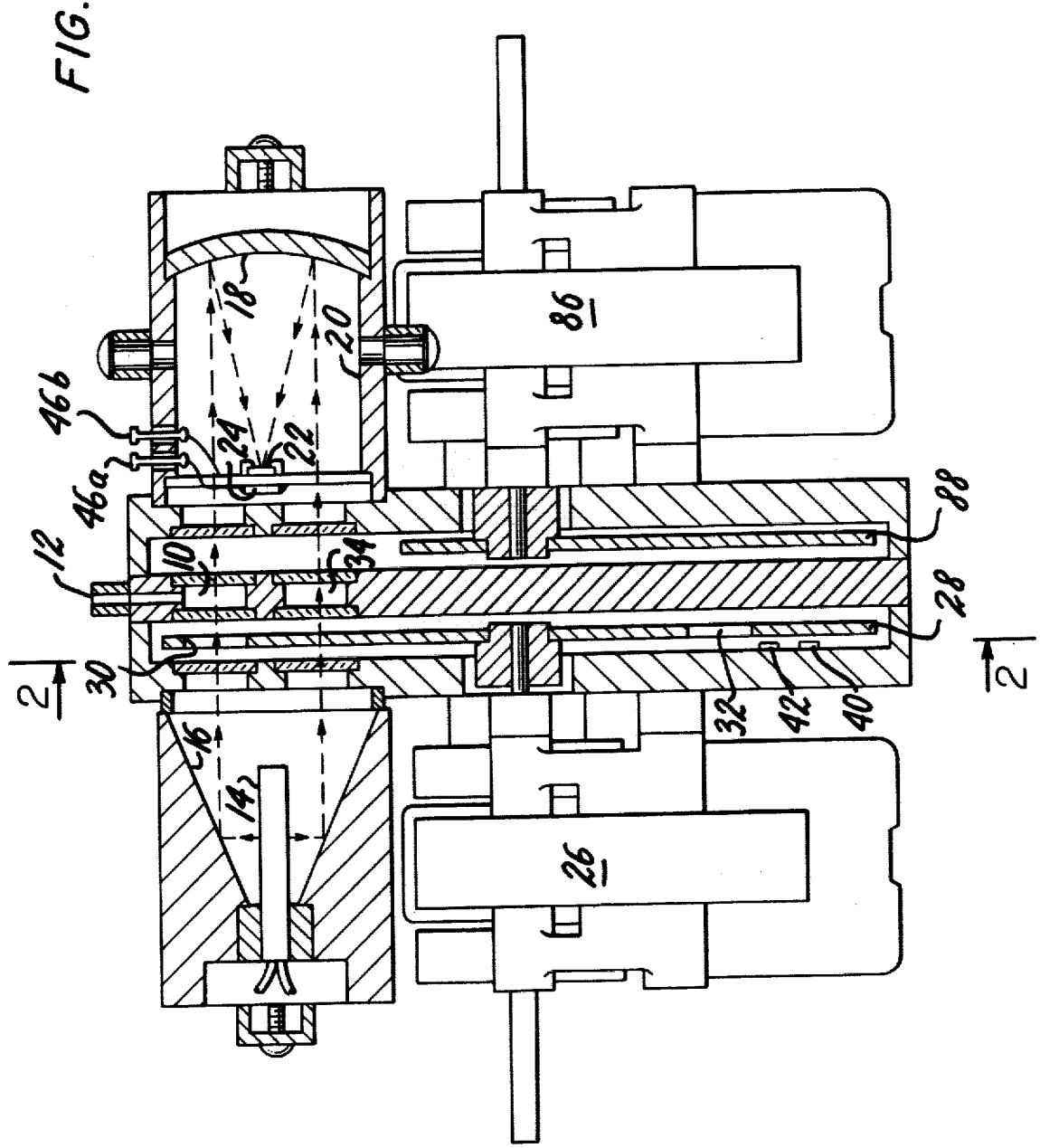
FIG. 1 is a front elevation, partly in section, of the optical-mechanical components of the preferred embodiment.

As shown in FIG. 1, the analyzer has a sample chamber 10 which receives fluid samples through a supply pipe 12. Infrared light from a souce 14 is reflected from a source cavity 16 through the chamber 10 to a concave mirror 18 in a detector cavity 20 on the opposite side of the sample chamber from the source. The mirror 18 directs the infrared light to a pair of filters 22 and detectors 24 in the detector chamber, only one of the filters and detectors being shown in FIG. 1 because they are divided along the plane of the figure.

A motor 26 rotates a chopper disc 28 in the path of the light from the source to the detectors to alternately position one of several apertures 30 in alignment with the sample chamber 10 for transmission of the light to the detectors through the sample chamber 10 and, alternately, one of several other apertures 32 in alignment with a reference chamber 34 which is positioned between the source and detector cavities and in correspondence with the split between the detectors 24 relative to the sample chamber. Each of the two detectors 24 thus alternately receives light from the source along the two optical paths through the sample chamber 10 and the reference chamber 34.

Figure 2:
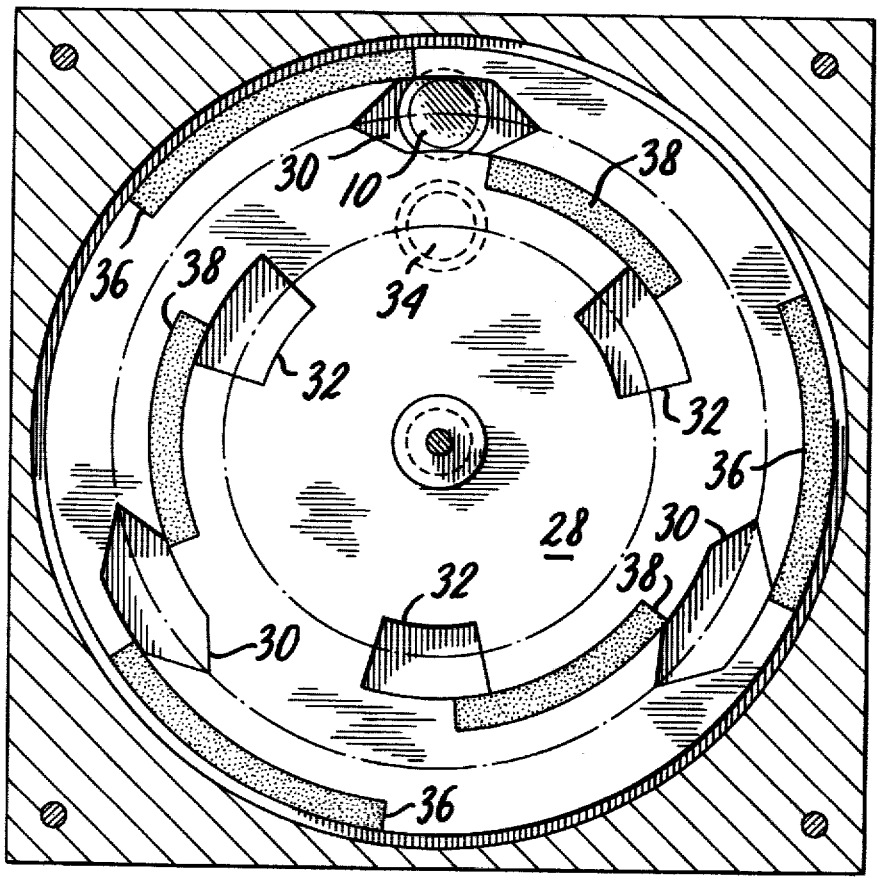
FIG. 2 is a side elevation of a portion of the mechanical components of the preferred embodiment.

FIG. 2 more clearly shows the alternate arrangement of the several apertures 30,32 in the chopper disc 28. FIG. 2 also shows two, alternating sequences of reflecting strips 36,38 which are arranged about the chopper disc over the intervals between the apertures 30,32.

A pair of light and photoelectric devices 40,42 shown in FIG. 1 detect the reflective strips 36,38, respectively, to provide alternate synchronizing signals corresponding to the alternate alignment of an aperture 30 with the sample chamber 10 and an aperture 32 with the reference chamber 34. The photoelectric devices 40,42 are therefore identified as the sample sync pickup and reference sync pickup in FIG. 3.

FIG. 3 further indicates a zero sync device 44 which responds to the simultaneous presence of both a sample sync signal and a reference sync signal to indicate that the chopper disc has rotated to an intermediate position in which neither of the apertures 30,32 is aligned with its respective chamber. (The positions of the reflective strips 36,38 shown in FIG. 2 do not seem to correspond exactly with their described function of indicating alignment of the apertures 30,32 with their respective chambers because of the high, 3300 RPM speed of preferred rotation of the chopper disc and consequent significant effect of electrical circuit delay. The high speed of chopper disc rotation is desired, however, to provide a rapidly alternating signal for more accurate intergration).

Each of the detectors 24 are shown in FIG. 3 and thus identified as 24a,24b in FIG. 3, only one of the detectors 24 having been shown in FIG. 1 because they are split along the plane of the figure and in parallel to the axis between chambers 10 and 34 to each receive equally the light passing along the separate optical paths through the chambers. Each detector 24a,24b is connected, respectively, by a lead 46a,46b to a preamplifier 48a,48b and other, identical circuitry 50a,50b. Only the circuitry 50a is therefore shown in detail for description.

The circuitry 50a has a zero clamp and amplifier device 52 which resets the output of the circuitry 50a to zero each time the zero sync device 44 indicates that the chopper disc 28 (FIG. 2) is in an intermediate position with neither aperture 30,32 aligned with its respective chamber and thus the absence of proper light along either optical path to the detectors. When, however, an aperture 30 is aligned with the sample chamber 10 (both shown in FIG. 2) as indicated by a signal from the sample sync pickup 40 alone, the signal from the sample sync pickup closes a switch 54. In the alternate interval when an aperture 32 is aligned with the reference chamber 34 (both shown in FIG. 2), the signal from the reference sync pickup 42 alone similiarly closes a switch 56.

The signal from the detector 24a is amplified by the zero clamp and amplifier 52, except when clamped to zero in the interval between aperture alignment and inverted by inverting amplifier 58 only in the path which is closed by switch 54 upon alignment of an aperture 30 with the sample chamber 10. The signal from the detector along the path to switch 56 is not inverted so that the signals from switches 54 and 56 corresponding to light through the alternate optical paths through the sample and reference chambers have opposite polarity.

The signal from the switch 56 is also provided to an automatic gain control amplifier 60 which functions as a comparitor with a regulated voltage supply input at the terminal 62. The signal from amplifier 60 is adjusted by an automatic gain control error detector 63 and supplied to an automatic gain control amplifier 64 to adjust the gain of the signal from the detector 24a according to the regulated voltage supply and reference chamber absorption each time switch 56 closes. The reference chamber is sealed and the voltage supply fixedly regulated to thus reset the processing circuitry 50a periodically during analyzer operation.

The circuitry 50b is identical to the circuitry 50a just described. It therefore requires no further description. The corresponding operation of the circuitry 50a,50b on the signals from the respective detectors 24a,24b, will, however, now be briefly described with reference to circuitry 50a because it corresponds to the operation of the device disclosed in the beforementioned U.S. Pat. No. 4,069,420.

When light from the source 14 passes along the optical path through an aperture 30 and sample chamber 10 to the detector 24a (and 24b), the fluid in the sample chamber 10 absorbs some of the light. The absorption varies with the wavelength, with the various constituants absorbing more of the light at certain wavelengths characteristic of the respective constituents and in an amount proportional to the concentration of the constituants in the fluid. The filter 22 (FIG. 1) associated with the detector 24a limits the transmission of light to the detector 24a to a wavelength band at the absorption characteristic wavelength of the constituent selected for analysis, while the filter 22 associated with detector 24b limits light to its detector to a different wavelength band at which the absorption at least approximates the background absorption of the other constituants of the fluid. The intensity of the light in the wavelength band which is passed through the sample chamber 10 then produces an electrical signal in detector 24a of a level corresponding to the concentration of the selected constituant of the fluid sample to be analyzed. This signal is then amplified by amplifiers 48a, 64 and 52, inverted by amplifier 58a and passed to an output terminal 66 through switch 54 which is then closed by the signal from the sample sync pickup 40. Similiarly, light in the filter pass band and passing through the reference chamber 34 when the chopper disc 28 is rotated to position as aperture 32 in alignment with the chamber 34 produces a signal in detector 24a which is amplified, but not inverted and passed to the output terminal 66 through the switch 56 which is then closed by the signal from the reference sync pickup 42.

The alternating, opposite polarity signals at output terminal 66 are then integrated in an integrating amplifier 68 to provide a signal proportional to the amount of absorption by the fluids in the sample and reference chambers in the pass band of the filters. Using the alternate signals in this way, particularly at the high rate of alternation provided by the preferred rapid rotation of the chopper disc, provides a highly accurate difference signal which is reset to zero by the zero clamp and amplifier 52 in the inverval between light transmission and at a level adjusted to each transmission through the reference chamber for still further accuracy.

The operation of detector 24b, amplifier 48b and circuitry 50b, which departs from the structure shown in U.S. Pat. No. 4,069,420, is similiar to that just described for detector 24a, amplifier 48a and circuitry 50a to require no further description, but different from the non-characteristic wavelength of the filter 22 associated with detector 24b. The signal from the corresponding output terminal 66' is then provided to an integrating amplifier 68' in further correspondence with the previous description.

Both integrating amplifiers 68, 68', however, invert their input-to-output signals. With a calibration or cal switch arm 70a in the position shown, the inverted output from integrating amplifier 68' is provided to the input of integrating amplifier 68 to thus provide an additional signal to opposite polarity to that from terminal 66 for difference integration in integrating amplifier 68. The signal from detector 24b is thus subtracted from the signal from detector 24a.

The combined signal from integrating amplifier 68 is linearized in linearizer 72, adjusted in span potentiometer 74, and carried through arm 70b of the cal switch and null check switch 76 to a display 78 which will indicate the concentration of a selected constituent of the fluid in the sample chamber. Several other adjustment potentiometers are indicated in FIG. 3 as cal pot 80 which is arranged for contact with the cal switch arm 70b, a neutral gain potentiometer 82 between amplifier 68' and the null check switch 76, and a null set potentiometer 84 which provides a further signal to output terminal 66 of the circuitry 50a, there being, therefore, a corresponding null set potentiometer (not shown) in the circuitry 50b.

Cal switch arms 70a, 70b are ganged to a further switch arm 70c. When closed, switch arm 70c activates a motor 86 which rotates a calibration wedge or shutter 88 (FIG. 1) into the optical paths from the source to the detectors. The wedge or shutter 88 then blocks the light to an extent preset to provide an intensity to detectors which, when the sample chamber is empty, equals the maximum attenuation of the light from 100% of the selected constituent in the fluid to be analyzed, this operation of the cal wedge or shutter 88 being the same as that disclosed in U.S. Pat. No. 4,069,420.

OPERATION

The operation of the device can now be described, but for convenience, the devices arranged from detector 24a to circuitry 50a will be referred to as the measurement channel processor and the devices from detector 24b to circuitry 50b will be referred to as the neutral channel processor, it being noted that these processor channels are different from the two optical paths through the sample chamber 10 and reference chamber 34 shown in FIG. 1 and related circuit channels through the switches 54, 56.

The filter 22 associated with the detector 24a is selected to pass a band of wavelengths centered at the absorption characteristic of the constituent of the fluid in the sample chamber selected to be analyzed. The level of the signal in the measurement channel from the detector 24a is thus proportional to the concentration of the selected constituent on a background level of the absorption of other constituants of the fluid to be analyzed. The filter 22 associated with detector 24b has a different pass band at a wavelength different from that of the characteristic of the constituent to be analyzed. This pass band is preferably selected at a wavelength at which the absorption of the constituent to be analyzed is least so the level of the signal from detector 24b most closely corresponds to the level of the signal in detector 24a from the absorption of the light by constituents of the fluid other than the constituent selected for analysis. This is the background level from which the absorption of the selected constituent at its characteristic wavelength departs. The neutral channel detector 24b thus provides a signal at least approximating the background absorption, while the measurement channel signal from detector 24a corresponds to the absorption of the selected constituent and the background.

The inversion of the neutral channel signal in integrating amplifier 68' and supply of this signal to the input of further inverting integrating amplifier 68 thus subtracts the background signal of the neutral channel from the combined concentration-indicating and background signal of the measurement channel to provide as the output of integrating amplifier 68 to the display 78 a difference signal from which at least much of the background signal has been subtracted. Small concentration-indicating signal components are then easier to detect more accurately from the combined signal with the reduced background component. Because many liquids have a high background absorption, removing the high background level from the concentration-indicating signal particularly adapts the analyzer for analyzing liquids.

Even with the cancellation (subtraction) of optical variations via the two optical paths through the sample and reference chambers and with the cancellation (subtraction) of the background level from the signal from the measurement and neutral channels, however, highly accurate determination of the absolute value of the concentration-indicating signal which is necessary to indicate the corresponding absolute value of the concentration of the selected constituent requires frequent calibration of the analyzer to compensate for internal changes in its operation, for example from electrical component aging and temperature changes. In the past, this was done exclusively by introducing into the analyzer standard fluids of known maximum and minimum concentration of the selected constituent and then adjusting the analyzer to indicate the known zero and full span concentrations of the standard fluids. Such standard gases, for example 100% $CO_2$, are reasonably readily available, but such standard liquids are frequently more difficult to obtain and maintain. With the analyzer here described, such calibration of the analyzer with standard fluids can be done less frequently, with intermediate adjustments of the analyzer performed with a staple (readily available) fluid, preferably air.

For this unique adjustment or calibration of the analyzer with the staple fluid, the sample chamber 10 is emptied of other fluid and preferably flushed and then filled with the staple fluid clean air. The null check switch 76 is then moved from the position in FIG. 3 for connecting the display 78 directly to the neutral gain potentiometer 82. The null set potentiometer (not shown) in the neutral channel circuitry 50b corresponding to the null set potentiometer 84 shown in the measurement channel circuitry 50a is then adjusted to zero the display 78. This corresponds to a zero background reading of the staple fluid which was selected to have a very low, zero or near-zero absorption at all wavelengths relative to the background and characteristic absorption of the fluid to be analyzed. The null check switch 76 is then returned to the position shown in FIG. 3 and the null set potentiometer 84 also adjusted to zero which again corresponds to the immeasurably low absorption of the staple fluid. Both the neutral and measurement channels are thus adjusted to indicate properly the zero absorption of the staple fluid to remove zeroing errors in the components of the analyzer.

The cal switch arms 70a, 70b, 70c are then moved from the position shown in FIG. 3. This open circuits the neutral channel, actuates the calibration motor 86 and wedge 88, and connects the display 78 to the calibration potentiometer 80.

Because of the zero absorption of the staple fluid, the wedge 88 then produces a full-scale optical signal. The span potentiometer 74 is then adjusted to indicate, through the cal potentiometer 80, a full scale reading on the display 78. The switch arms 70a, 70b, 70c are then returned to the positions shown in FIG. 3, the analyzer now having been adjusted with only the staple fluid to compensate for internal changes affecting both zero and full scale concentration measurements.

Less frequently than would otherwise be required, the analyzer will also require adjustment to background but zero selected constituent characteristic absorption and full scale (span) background and characteristic absorption. This adjustment is done independently of the staple-fluid adjustment just described using specially prepared zero and span standard fluids of known zero and full span absorption.

For the standard-fluid adjustment, the zero standard fluid is first put in the sample chamber with the circuit arrangement shown in FIG. 3, and the neutral gain potentiometer 82 adjusted to obtain a zero reading on the display 78. Since the zero fluid has only background absorption, this adjusts the analyzer to fully cancel (subtract) the background signal component from the combined signal of the measurement and neutral channels at the display.

The span standard fluid is then substituted in the sample chamber, again with the circuit arrangement shown in FIG. 3. The span potentiometer 74 is then adjusted to indicate full span on the display which corresponds to the known full-span background and selected constituent absorption of the span standard fluid. The analyzer is thus separately adjusted for accuracy when fluids of known, finite absorption are in the analyzer for accurately analyzing fluids of unknown concentration of the selected constituent.

Of course, both the staple-fluid and standard-fluid adjustments can be done together. It is then appropriate to first perform the staple-fluid adjustment and then the standard-fluid adjustment. Since both adjustments set the span potentiometer 74, compensation for any change from the first, staple-fluid adjustment of the span potentiometer to its second, standard-fluid adjustment must be provided. For this, in the combined staple—and standard—fluid adjustments, the staple fluid is reintroduced into the sample chamber, the cal switch arms actuated to connect arm 70b to the calibration potentiometer 80, and the calibration potentiometer 80 adjusted to re-zero the display 78 to indicate the zero absorption of the staple fluid. When the cal switch arms are thereafter returned to the positions shown in FIG. 3, the signal bleed through the cal potentiometer 80 retains this final adjustment.

The preferred embodiment now described merely illustrates one form of the invention which is a fluid concentration analyzer including the separate measurement and neutral signal-processing channels and the separate staple—and standard—fluid adjustments. Other embodiments having variations and modifications as may occur to those in the art are contemplated as being within the scope of the invention particularly because the fluids for analysis may be either liquid or gas possibly to require such variations and modifications.

We claim:

1. An optical fluid analyzer, comprising:

a sample chamber for receiving a fluid sample;

optical means for providing an optical signal of the concentration in the fluid of a selected constituent of the fluid in the sample chamber on a background from the other constituents of the fluid;

neutral channel processing means for converting the optical signal into an electrical signal at least approximating the background portion of the optical signal;

measurement channel processing means for converting the optical signal into an electrical signal of the concentration of the selected constituent and the background; and output means combining the electrical signals for subtracting the neutral channel signal at least approximating the background from the measurement channel signal of concentration and background, whereby at least much of the background portion of the signal is removed from the combined signal for more accurately extracting the concentration-indicating signal from the combined signal is further electrical signal processing.

2. An optical fluid analyzer as in claim 1 wherein the optical means comprises a light source from which light is absorbed by the selected constituent of the fluid in the sample chamber at a characteristic wavelength proportionally to the concentration of the selected constituent in the fluid and by the other constituents of the fluid, wherein the neutral channel processing means comprises first filter and detector means for response to the light absorption at a wavelength other than the characteristic wavelength of the selected constituent, and wherein the measurement channel processing means comprises second filter and detector means for response to the light absorption at the characteristic wavelength of the selected constituent.

3. An optical fluid analyzer, comprising:

a sample chamber for receiving a fluid sample;

optical means for providing an optical signal indicating the extent of optical absorption of a fluid in the sample chamber at a wavelength at which a selected constituent of the fluid to be analyzed has a characteristic optical absorption, whereby to indicate from the extent of absorption the concentration of the selected constituent of the fluid to be analyzed;

processing means for converting the optical signal into an electrical signal;

first adjusting means in the processing means for setting the electrical signal to zero when a staple fluid which does not optically absorb significantly in relation to the fluid to be analyzed is in the sample chamber, whereby to compensate for variations in the analyzer operation with only the staple fluid as often as desired;

separate, second adjusting means in the processing means for setting the electrical signal to zero when a standard fluid known to optically absorb correspondingly to the fluid to be analyzed except for the absorption of the selected constituent is in the sample chamber, whereby to preset the analyzer to provide a zero electrical signal from the processing means when there is no optical absorption at the wavelength of the optical means; and means for introducing the staple fluid, standard fluid, and fluid to be analyzed into the sample chamber.

4. An optical fluid analyzer as in claim 3 wherein the optical signal has a background level from the other constituents of the fluid to be analyzed when the fluid to be analyzed is in the sample chamber, and wherein the processing means comprises:

neutral channel processing means for converting the optical signal into an electrical signal at least approximating the background portion of the optical signal;

measurement channel processing means for converting the optical signal into an electrical signal of the concentration of the selected constituent and the background; and output means combining the electrical signals for subtracting the neutral channel signal at least approximating the background from the measurement channel signal of concentration and background, whereby at least much of the background portion of the signal is removed from the combined signal for more accurately extracting the concentration-indicating signal from the combined signal in further electrical signal processing.

5. An optical fluid analyzer as in claim 1, 3 or 4 wherein the optical means further comprises: a reference chamber for receiving a reference fluid of known optical absorption; a light source from which light is absorbed by the selected constituent of the fluid in the sample chamber at a characteristic wavelength proportionally to the concentration of the selected constituent in the fluid and by the other constituents of the fluid; means for defining a first optical path from the light source into the sample chamber and a second optical path from the light source into the reference chamber; means for alternately passing light from the source along the first and second optical paths; first filter and detector means for response to the light absorption at a wavelength other than the characteristic wavelength of the selected constituent of light from both the sample and reference chambers; and second filter and detector means for response to light absorption at the characteristic wavelength of the selected constituent of light from both the sample and reference chambers.

* * * * *